(12) United States Patent
Song et al.

(10) Patent No.: US 10,314,562 B2
(45) Date of Patent: Jun. 11, 2019

(54) ULTRASONIC PROBE AND METHOD OF MANUFACTURING THE SAME

(71) Applicant: SAMSUNG MEDISON CO., LTD., Gangwon-Do (KR)

(72) Inventors: Kyung Hun Song, Seongnam-si (KR); Jae Moon Jo, Seongnam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 237 days.

(21) Appl. No.: 14/578,320

(22) Filed: Dec. 19, 2014

(65) Prior Publication Data
US 2015/0173712 A1     Jun. 25, 2015

(30) Foreign Application Priority Data

Dec. 20, 2013    (KR) ........................ 10-2013-0159832

(51) Int. Cl.
     *A61B 8/00*      (2006.01)
     *B06B 1/06*      (2006.01)
     *G10K 11/00*     (2006.01)

(52) U.S. Cl.
CPC .......... *A61B 8/4444* (2013.01); *A61B 8/4483* (2013.01); *B06B 1/06* (2013.01); *G10K 11/002* (2013.01); *B06B 1/0685* (2013.01); *Y10T 29/42* (2015.01)

(58) Field of Classification Search
None
See application file for complete search history.

(56) References Cited

U.S. PATENT DOCUMENTS

| | | | |
|---|---|---|---|
| 7,105,986 B2* | 9/2006 | Wildes | A61B 8/546 310/327 |
| 2006/0186765 A1 | 8/2006 | Hashimoto | |
| 2007/0276248 A1* | 11/2007 | Saito | A61B 8/546 600/459 |
| 2008/0243001 A1* | 10/2008 | Oakley | A61B 8/4281 600/459 |
| 2012/0238880 A1* | 9/2012 | Davidsen | B06B 1/0629 600/459 |

FOREIGN PATENT DOCUMENTS

| | | |
|---|---|---|
| EP | 1 671 588 A1 | 6/2006 |
| EP | 2 638 861 A1 | 9/2013 |

(Continued)

OTHER PUBLICATIONS

Extended European Search Report issued in corresponding European Patent Application No. 14185898.5, dated Sep. 10, 2015.

(Continued)

*Primary Examiner* — Tse W Chen
*Assistant Examiner* — Patrick M Mehl
(74) *Attorney, Agent, or Firm* — Morgan Lewis & Bockius LLP

(57) ABSTRACT

Provided are an ultrasonic probe and a method of manufacturing the same. The ultrasonic probe includes: a matching layer; a piezoelectric layer that is disposed on a bottom surface of the matching layer and generates ultrasonic waves; and a backing layer that is disposed on a bottom surface of the piezoelectric layer and includes plate-shaped carbon allotropes and a backing material provided between the plate-shaped carbon allotropes.

16 Claims, 12 Drawing Sheets

(56) References Cited

FOREIGN PATENT DOCUMENTS

| | | |
|---|---|---|
| JP | 2006-102135 A | 4/2006 |
| JP | 4934300 B2 | 5/2012 |
| JP | 2013-027667 A | 2/2013 |
| WO | 2008-121238 A2 | 10/2008 |
| WO | WO-2013-009002 * 1/2013 | ............... A23B 7/02 |

OTHER PUBLICATIONS

European Patent Communication pursuant to Article 94(3) EPC issued in European Application No. 14 185 898.5 dated Mar. 20, 2018.

Office Action issued in Chinese Application No. 201410790420.4 dated Oct. 19, 2018, with English translation.

\* cited by examiner

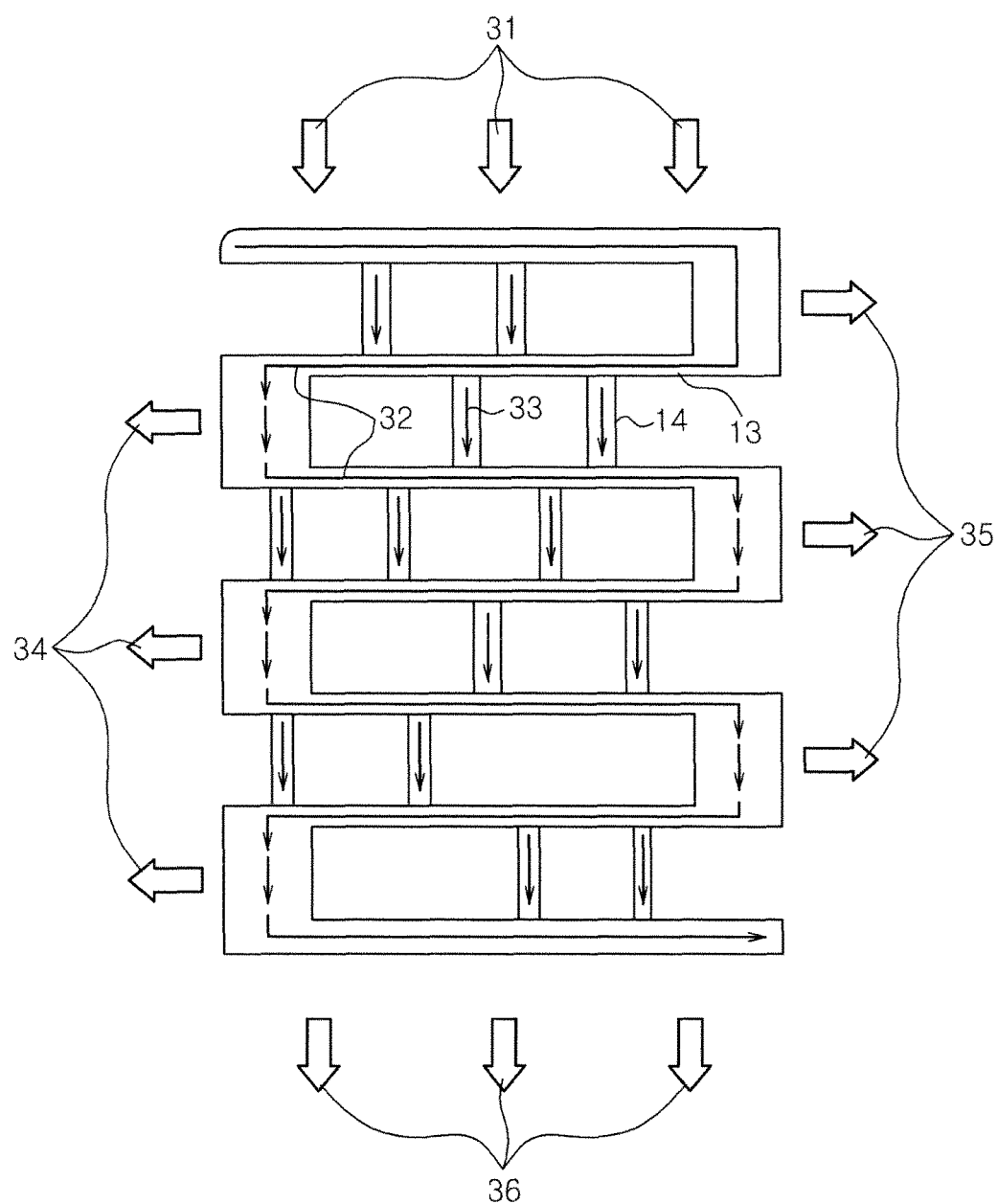

ULTRASONIC PROBE AND METHOD OF MANUFACTURING THE SAME

CROSS-REFERENCE TO RELATED APPLICATION

This application claims the benefit of Korean Patent Application No. P2013-0159832, filed on Dec. 20, 2013 in the Korean Intellectual Property Office, the disclosure of which is incorporated herein by reference.

BACKGROUND

1. Field

Embodiments of the present invention relate to an ultrasonic probe that is capable of maintaining sound absorption performance of a backing layer and effectively dissipating heat generated for reasons of converting energy of a piezoelectric layer and for other reasons, and a method of manufacturing the ultrasonic probe.

2. Description of the Related Art

Ultrasonic probes are apparatuses that radiate ultrasonic signals onto a target part of a body from a body surface of an object to be inspected and obtain a tomogram of a soft tissue or an image of blood flow of the soft tissue using information regarding reflected ultrasonic signals (ultrasonic echo signals) in a noninvasive manner.

In comparison with other image probes, such as X-ray probes, X-ray computerized tomography (CT) scanners, magnetic resonance imaging (MRI) probes, and nuclear medicine probes, ultrasonic probes are small-sized and cheap, can display an image in real time, and have high safety due to lack of radiation exposure, such as X-rays. Thus, ultrasonic probes are widely used in heart, abdominal, urinary, and ob-gyn diagnoses.

An ultrasonic probe includes an ultrasonic probe that transmits ultrasonic signals to the object to be inspected and receives ultrasonic echo signals reflected from the object to be inspected so as to obtain an ultrasonic image of the object to be inspected.

The ultrasonic probe includes a transducer. Here, the transducer may include a piezoelectric layer that transforms between electrical signals and sound signals while a piezoelectric material vibrates, a matching layer that reduces a difference in acoustic impedance between the piezoelectric layer and the object to be inspected so that ultrasonic waves generated in the piezoelectric layer can be transmitted to the object to be inspected as much as possible, a lens layer that focuses ultrasonic waves proceeding toward the front of the piezoelectric layer on a particular place, and a backing layer that prevents image distortion by blocking progression of the ultrasonic waves toward the rear of the piezoelectric layer.

Research on transferring heat generated due to miniaturization and high-performance of the piezoelectric layer within the ultrasonic probe toward the rear of the ultrasonic probe (not toward the front of the ultrasonic probe) or to cool heat has been recently done.

SUMMARY

Therefore, it is an aspect of the present invention to provide an ultrasonic probe that includes plate-shaped carbon allotropes and a backing layer formed by providing an acoustic material between the plate-shaped carbon allotropes, and a method of manufacturing the ultrasonic probe.

Additional aspects of the invention will be set forth in part in the description which follows and, in part, will be obvious from the description, or may be learned by practice of the invention.

In accordance with one aspect of the present invention, an ultrasonic probe includes: a matching layer; a piezoelectric layer that is disposed on a bottom surface of the matching layer and generates ultrasonic waves; and a backing layer that is disposed on a bottom surface of the piezoelectric layer and includes plate-shaped carbon allotropes and a backing material provided between the plate-shaped carbon allotropes.

Support frames of the plate-shaped carbon allotropes may be formed perpendicular to the piezoelectric layer, and the support frames of the plate-shaped carbon allotropes may be formed in a different position from that of a support frame on an adjacent layer.

The backing material provided between the carbon allotropes may each have the same acoustic impedance in each layer, and the backing material may be provided so that the acoustic impedance of the backing material provided between the carbon allotropes is reduced from a top surface to a bottom surface of the backing layer, and the backing material may be provided so that the acoustic impedance of the backing material provided between the carbon allotropes increases from the top surface to the bottom surface of the backing layer.

The plate-shaped carbon allotropes may be one selected from the group consisting of carbon nanotubes (CNTs), graphene, and graphite or may be a synthetic material of the carbon allotropes and a metal.

In accordance with another aspect of the present invention, a method of manufacturing an ultrasonic probe includes: disposing a matching layer; disposing a piezoelectric layer that generates ultrasonic waves, on a bottom surface of the matching layer; forming a backing layer by providing a backing material between plate-shaped carbon allotropes; and disposing the backing layer on a bottom surface of the piezoelectric layer.

BRIEF DESCRIPTION OF THE DRAWINGS

These and/or other aspects of the invention will become apparent and more readily appreciated from the following description of the embodiments, taken in conjunction with the accompanying drawings of which:

FIG. 4 is a conceptual view illustrating a state in which heat generated in the piezoelectric layer is dissipated by the plate-shaped carbon allotropes, in accordance with an embodiment of the present invention;

DETAILED DESCRIPTION

Figure 1:
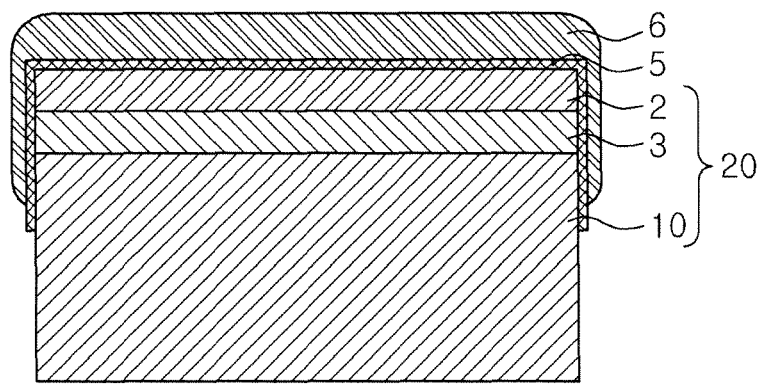
FIG. 1 is a cross-sectional view of a acoustic module within an ultrasonic probe in accordance with an embodiment of the present invention.

Reference will now be made in detail to the embodiments of the present invention, examples of which are illustrated in the accompanying drawings, so that one of ordinary skill in the art can easily understand and embody the present invention through the embodiments. However, in the description of the present invention, certain detailed explanations of related art are omitted when it is deemed that they may unnecessarily obscure the essence of the invention.

Since later-described terms are defined in consideration of the functions of the present invention, they may vary according to users' and operators' intentions or practice. Hence, the terms must be interpreted based on the contents of the entire specification, and if there are no specific definitions of the terms, the terms must be interpreted by one of ordinary skill in the art in a commonly-recognized meaning.

Furthermore, although configurations of embodiments that are selectively described are illustrated as a single combined configuration in the drawings, unless the configurations are described, if inconsistency in description is not obvious to one of ordinary skill in the art, they must be interpreted so that the configurations can be freely combined with each other.

Hereinafter, an ultrasonic probe 1 in accordance with an embodiment of the present invention will be described with reference to the accompanying drawings.

FIG. 1 is a cross-sectional view of the ultrasonic probe 1 in accordance with an embodiment of the present invention.

As illustrated in FIG. 1, the ultrasonic probe 1 may include a acoustic module 20 configured of a piezoelectric layer 3, a backing layer 10 disposed on a bottom surface of the piezoelectric layer 3, and a matching layer 2 disposed on a top surface of the piezoelectric layer 3, a protective layer 5 that covers a top surface of the acoustic module 20 and a part of sides of the acoustic module 20, and a lens layer 6 that covers a top surface and sides of the protective layer 5.

The acoustic module 20 may also be referred to as an ultrasonic transducer. A magnetostrictive ultrasonic transducer that uses magnetostrictive effects of a magnetic substance, a capacitive micromachined ultrasonic transducer that transmits and receives ultrasonic waves using vibration of several hundreds of or several thousands of micromachined thin films, or a piezoelectric ultrasonic transducer that uses a piezoelectric effect of a piezoelectric material may be used as the ultrasonic transducer. Hereinafter, the piezoelectric ultrasonic transducer will be described as an embodiment of a transducer.

The effects that, if a mechanical pressure is applied to a predetermined material, a voltage is generated and if a voltage is applied to the predetermined material, mechanical deformation occurs, are referred to as a piezoelectric effect and an inverse piezoelectric effect, and a material having these effects is referred to as a piezoelectric material. That is, the piezoelectric material is a material that transforms electric energy into mechanical vibration energy or vice versa.

The ultrasonic probe 1 may include the piezoelectric layer 3 that is formed of the piezoelectric material that transforms an electrical signal applied to the piezoelectric layer 3 into mechanical vibration so as to generate ultrasonic waves.

The piezoelectric material that constitutes the piezoelectric layer 3 may include a ceramic of lead zirconate titanate (PZT), a PMN-PT monocrystal formed of a solid solution of lead magnesium niobate (PMN) and lead titanate (PT), or a PZNT monocrystal formed of a solid solution of lead zinc niobate (PZN) and PT. In addition, various materials for transforming electrical signals into mechanical vibration may be used as an example of the piezoelectric material that constitutes the piezoelectric layer 3.

Also, the piezoelectric layer 3 may be arranged in a single layer structure or a multilayer stack structure. The piezoelectric layer 3 having a stack structure can generally more easily adjust impedance and voltages, thereby obtaining good sensitivity, energy conversion efficiency, and a soft spectrum. In addition, various structures may be used as an example of the structure of the piezoelectric layer 3 for improving the performance of the piezoelectric layer 3.

The backing layer 10 is disposed on the bottom surface of the piezoelectric layer 3, absorbs the ultrasonic waves that are generated in the piezoelectric layer 3 and proceed toward the rear of the piezoelectric layer 3, thereby blocking progression of the ultrasonic waves toward the rear of the piezoelectric layer 3. Thus, the backing layer 10 can prevent distortion of an image. The backing layer 10 may be manufactured as a plurality of layers so as to improve an attenuation or blocking effect of the ultrasonic waves. In addition, various structures may be used as an example of the structure of the backing layer 10 so as to improve the attenuation or blocking effect of the ultrasonic waves.

The matching layer 2 may be disposed on the top surface of the piezoelectric layer 3. The matching layer 2 matches acoustic impedance of the piezoelectric layer 3 and the object to be inspected by reducing a difference in acoustic impedance between the piezoelectric layer 3 and the object to be inspected so that ultrasonic waves generated in the piezoelectric layer 3 can be efficiently transferred to the object to be inspected. To this end, the matching layer 2 can be provided to have an intermediate value between acoustic impedance of the piezoelectric layer 3 and acoustic impedance of the object to be inspected.

The matching layer 2 may be formed of glass or a resin. In addition, various materials may be used as an example of a material used to form the matching layer 2 so as to match acoustic impedance of the piezoelectric layer 3 and the object to be inspected.

Also, the matching layer 2 may be configured of a plurality of matching layers 2 so that acoustic impedance varies from the piezoelectric layer 3 toward the object to be inspected stepwise, and materials for the plurality of matching layers 2 may be different. In addition, various structures may be used as an example of the structure of the matching layer 2 so that acoustic impedance varies stepwise.

Also, the piezoelectric layer 3 and the matching layer 2 may be processed in the form of a 2D array having a matrix shape through a dicing process or in the form of a one-dimensional (1D) array.

The protective layer 5 may be disposed to cover a top surface of the matching layer 2 and a part of sides of the acoustic module 20. The protective layer 5 may include a chemical shield that may protect internal parts of the ultrasonic probe 1 from water or medicine used in disinfection by coating or depositing a conductive material on the surface of a film having moisture tolerance and chemical resistance. The chemical shield may be formed by performing parylene coating on the top surface of the matching layer 2 and a part of sides of the acoustic module 20 using a polymer film. Also, the chemical shield may be formed by applying a cross-sectional sputter onto the polymer film.

Also, the protective layer 5 may include a radio frequency (RF) shield that may prevent outflow of high frequency components that may be generated in the piezoelectric layer 3 and that may block inflow of high frequency signals. In addition, various configurations for blocking inflow/outflow of high frequency components may be used as an example of a configuration of the protective layer 5.

The lens layer 6 may be disposed to cover the top surface and sides of the protective layer 5. A low attenuation material may be used to form the lens layer 6 so as to prevent ultrasonic signals generated in the piezoelectric layer 3 from being attenuated. For example, a low viscosity epoxy resin DER322 or epoxy, such as DEH24, may be used to form the lens layer 6. In addition, various materials for preventing the ultrasonic signals from being attenuated may be used as an example of the material for the lens layer 6. In this way, the lens layer 6 is manufactured using the low attenuation material so that sensitivity of the ultrasonic signals can be improved.

Also, the lens layer 6 may be disposed to cover a part of a kerf of the acoustic module 20 that is a part of sides of the acoustic module 20, thereby reducing crosstalk.

Hereinafter, the backing layer 10 including plate-shaped carbon allotropes 11, and the piezoelectric layer 3 in accordance with an embodiment of the present invention will be described with reference to FIG. 2.

Figure 2:
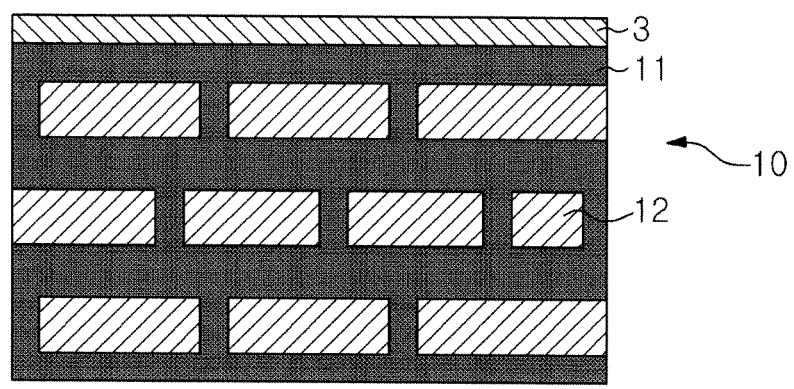
FIG. 2 is a cross-sectional view of a backing layer including plate-shaped carbon allotropes and a backing material, and a piezoelectric layer, in accordance with an embodiment of the present invention.

FIG. 2 illustrates a cross-section of the backing layer 10 including the plate-shaped carbon allotropes 11 and a backing material, and the piezoelectric layer 3.

The backing layer 10 may be disposed on the bottom surface of the piezoelectric layer 3 and may include the carbon allotropes 11 and the backing material. The backing layer 10 may absorb ultrasonic waves that are generated in the piezoelectric layer 3 or are reflected from the object to be inspected and proceed toward the rear of the piezoelectric layer 3, thereby blocking progression of the ultrasonic waves toward the rear of the piezoelectric layer 3. Thus, the backing layer 10 may prevent an image from being distorted.

The carbon allotropes 11 may absorb heat generated in the piezoelectric layer 3 disposed on the top surface of the backing layer 10 for reasons of generating ultrasonic waves or for other reasons, block progression of the generated heat toward the front of the piezoelectric layer 3, and may transfer the generated heat toward the rear of the backing layer 10 and dissipate heat.

A material used to form the carbon allotropes 11 may be carbon allotropes having high thermal conductivity. Allotropes are materials that are configured of an element of the same kind but have different molecular formulae or structures, i.e., simple substances that have the same atomic number but different neutron numbers. Allotropes are materials having the same chemical composition but different arrangement states or bonding forms of atoms. For example, the material used to form the carbon allotropes 11 may be carbon nanotubes (CNTs), graphene, or graphite.

In detail, the CNTs are a material in which hexagonal honeycombs including 1 carbon atom connected to 3 other carbon atoms form a tubular shape and which is configured of only carbon atoms having a diameter of several nanometers (a nanometer (1 nm)=one-billionth of a meter, or about one hundred-thousandth of the thickness of a human hair). Thermal conductivity of the CNTs is as excellent as diamond (5 times that of copper), and electric conductivity of the CNTs is much higher than electric conductivity of copper, and strength of the CNTs is 100 times that of steel having a same thickness. The CNTs may be categorized by their structures: single-wall nanotubes (SWNT), multi-wall nanotubes (MWNT), and bundle-type nanotubes (BTNT).

The graphene is a material that constitutes a two-dimensional planar structure in which carbon atoms are arranged in a hexagonal honeycomb shape. The graphene is so thin and transparent that it may not be seen with the naked eye, is configured of carbon having high chemical stability, and thus may have excellent electric conductivity. In detail, a thickness of the graphene is about 0.2 nm, and the graphene may have high physical and chemical stability. Also, it is known that the graphene conducts electricity 100 times better than copper and causes movement of electrons 100 times faster than that of monocrystalline silicon that is mainly used as a semiconductor. In particular, strength of the graphene is 200 times that of steel, and thermal conductivity of the graphene is twice or more that of diamond having high thermal conductivity, and the graphene may not lose an electrical property even when it is extended or bent owing to its high elasticity.

The graphite is allotropes of carbon having metallic gloss, has a dihexagonal crystalline structure and is porous and may have a hygroscopic property and adsorbability. Also, the graphite may have chemical stability, good heat resistance, good thermal shock resistance, and good corrosion resistance, and is a good conductor of electricity and heat and thus may have lubricity.

A thermal conductivity K of the carbon allotropes 11 configured of the CNTs, graphene, and graphite may be about 13.4 [W/mK]. The thermal conductivity K may be relatively higher than that of MP003 of about 0.74 [W/mK] and that of MP004 of about 0.458 [W/mK]. Thus, heat generated in the piezoelectric layer 3 can be effectively transferred to the rear of the ultrasonic probe 1 due to high thermal conductivity.

Also, the material used to form the carbon allotropes 11 may be a synthetic material of carbon allotropes and a metal in addition to the carbon allotropes. The synthetic material of carbon allotropes and the metal may be generated by melting the carbon allotropes and the metal or by alternately stacking the carbon allotropes and the metal on each of layers.

In addition, various materials that are used to transfer heat generated in the piezoelectric layer 3 to the rear of the ultrasonic probe 1 may be used as an example of the carbon allotropes 11.

Also, the carbon allotropes 11 may have a plate shape including main frames 13 of carbon allotropes and support frames 14 of the carbon allotropes. The plate shape of the carbon allotropes 11 may be formed by stacking the main frames 13 to be parallel to the piezoelectric layer 3 on each of the layers and by supporting the stacked main frames 13 using the support frames 14.

The shape of the carbon allotropes 11 will be described later in detail.

The backing material 12 is provided in an empty space formed by the plate-shaped carbon allotropes 11 placed in the backing layer 10. The backing material 12 may be used to attenuate ultrasonic waves that are generated in the piezoelectric layer 3 and proceed to the rear of the ultrasonic probe 1 and ultrasonic waves that are reflected and received from the object to be inspected so that these ultrasonic waves can be prevented from proceeding to the rear of the ultrasonic probe 1. Also, the backing material 12 may be used to attenuate vibration that occurs in the piezoelectric layer 3.

A variable for the backing material 12 that is used to attenuate ultrasonic waves and vibration that proceed to the rear of the ultrasonic probe 1 may be acoustic impedance or an attenuation value. Acoustic impedance may be one of variables for determining a matching condition so that sound energy of a human body can be efficiently supplied from a piezoelectric material.

$$Z=(\rho c)^{1/2}=\rho \upsilon \qquad \text{[Equation 1]}$$

Equation 1 shows an equation for calculating acoustic impedance. In Equation 1, Z is acoustic impedance, and p is density of a backing material, and c is elasticity of the backing material, and u is a sound speed.

In Equation 1, the acoustic impedance may be a repeated root of a value obtained by multiplying the density of the backing material and the elasticity of the backing material or may be a value obtained by multiplying the density of the backing material and the sound speed.

Also, the unit of acoustic impedance is [kg/m$^2$ s] and may be referred to as Rayl.

The backing material may be provided by filling epoxy, ceramic, or metal, or a combination of an epoxy powder, a ceramic powder, and a metal powder. Also, the epoxy powder, the ceramic powder, and the metal powder may be synthesized at a predetermined ratio and may be filled in the backing material. In addition, various materials for attenuating ultrasonic waves and vibration that proceed to the rear of the ultrasonic probe 1 may be used as an example of the backing material.

Also, the backing materials 12 having equal acoustic impedance or the backing materials 12 having different acoustic impedance may be filled in each of the layers. The backing materials 12 having different acoustic impedance to be filled in each of the layers will be described later.

Hereinafter, the plate-shaped carbon allotropes 11 in accordance with an embodiment of the present invention will be described with reference to FIGS. 3A through 3C.

Figure 3A:
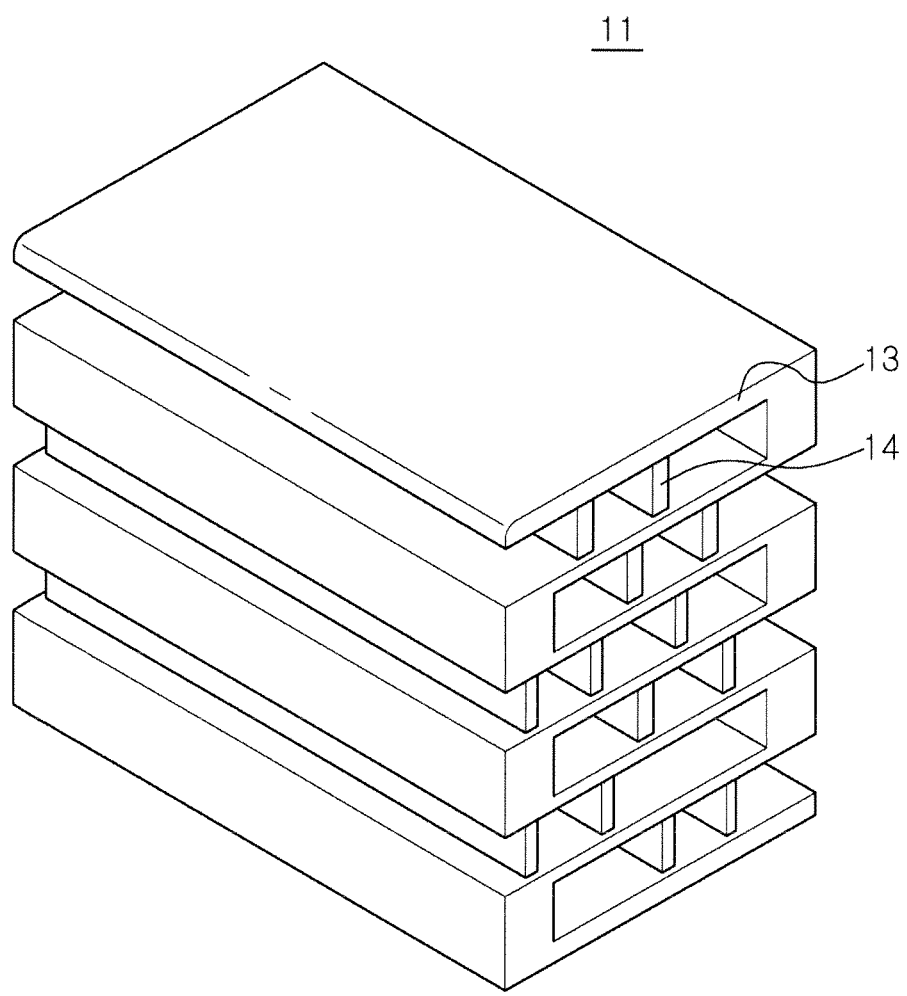
FIG. 3A is a perspective view illustrating an exterior of the plate-shaped carbon allotropes in accordance with an embodiment of the present invention.
Figure 3B:
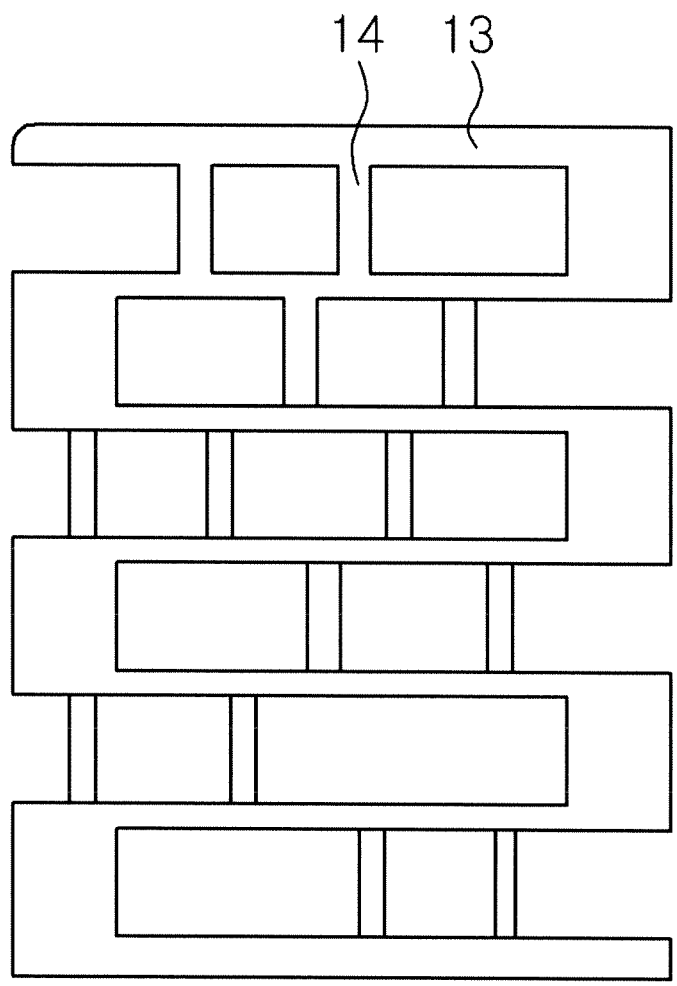
FIG. 3B is a cross-sectional view illustrating a front side of the plate-shaped carbon allotropes in accordance with an embodiment of the present invention.
Figure 3C:
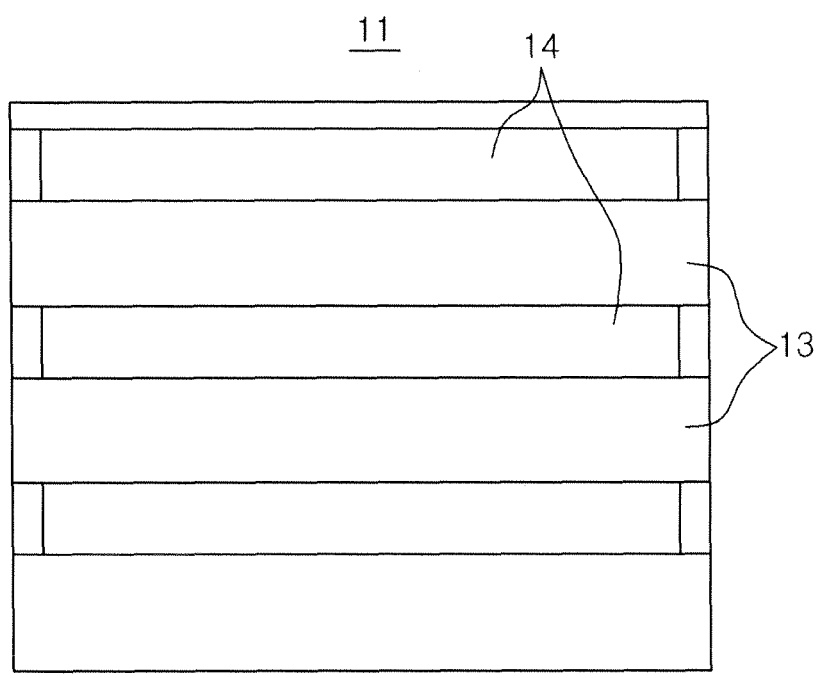
FIG. 3C is a cross-sectional view illustrating sides of the plate-shaped carbon allotropes in accordance with an embodiment of the present invention.

FIG. 3A illustrates an exterior of the plate-shaped carbon allotropes 11, and FIG. 3B is a cross-sectional view illustrating a front side of the plate-shaped carbon allotropes 11, and FIG. 3C illustrates sides of the plate-shaped carbon allotropes 11.

The plate-shaped carbon allotropes 11 may serve as a channel for absorbing heat generated in the piezoelectric layer 3, transferring the generated heat to the rear of the ultrasonic probe 1, and dissipating the transferred heat.

The plate-shaped carbon allotropes 11 may include the main frames 13 and the support frames 14.

The main frames 13 may be stacked on layers to be parallel to the backing layer 10 and may connect layers to which one of side surfaces of the main frames 13 are alternately adjacent to each other on each of the layers. Also, the thickness of each main frame 13 may be equal to or greater than ¼ times that of a wavelength of the ultrasonic waves generated in the piezoelectric layer 3.

The support frames 14 may be placed between the main frames 13 so as to maintain the shape of the main frames 13. The support frames 14 may be placed at a predetermined angle according to the purpose of the ultrasonic probe 1 and for other reasons. For example, the support frames 14 may also be placed perpendicular to the piezoelectric layer 3, as illustrated in FIGS. 3A through 3C.

Also, when the support frames 14 are placed perpendicular to the piezoelectric layer 3, the support frames 14 may be placed in a different position from that of the support frames 14 on an adjacent layer so as to disperse vibration transferred to the carbon allotropes 11. Also, support frames 14 at upper and lower sides adjacent to one support frame 14 may be placed in different positions.

The plate-shaped carbon allotropes 11 may be formed by performing a back grinding process, a dicing process, or an etching process.

In detail, the back grinding process is a process in which an unnecessary film on a rear surface of a wafer is removed and the rear surface of the wafer having a larger thickness than necessity is shaved off so as to reduce resistance and to improve thermal conductivity. The dicing process is a process in which a spindle that rotates at a high speed cuts using a diamond blade. The etching process is a process in which an oxide layer that is not covered with a photoresist is removed.

In addition, various methods may be used as an example of forming the carbon allotropes 11 in a plate shape.

Hereinafter, transferring heat generated in the piezoelectric layer 3 to the rear of the ultrasonic probe 1 and dissipating heat by the backing layer 10, in accordance with an embodiment of the present invention will be described with reference to FIGS. 4 and 5.

Figure 5:
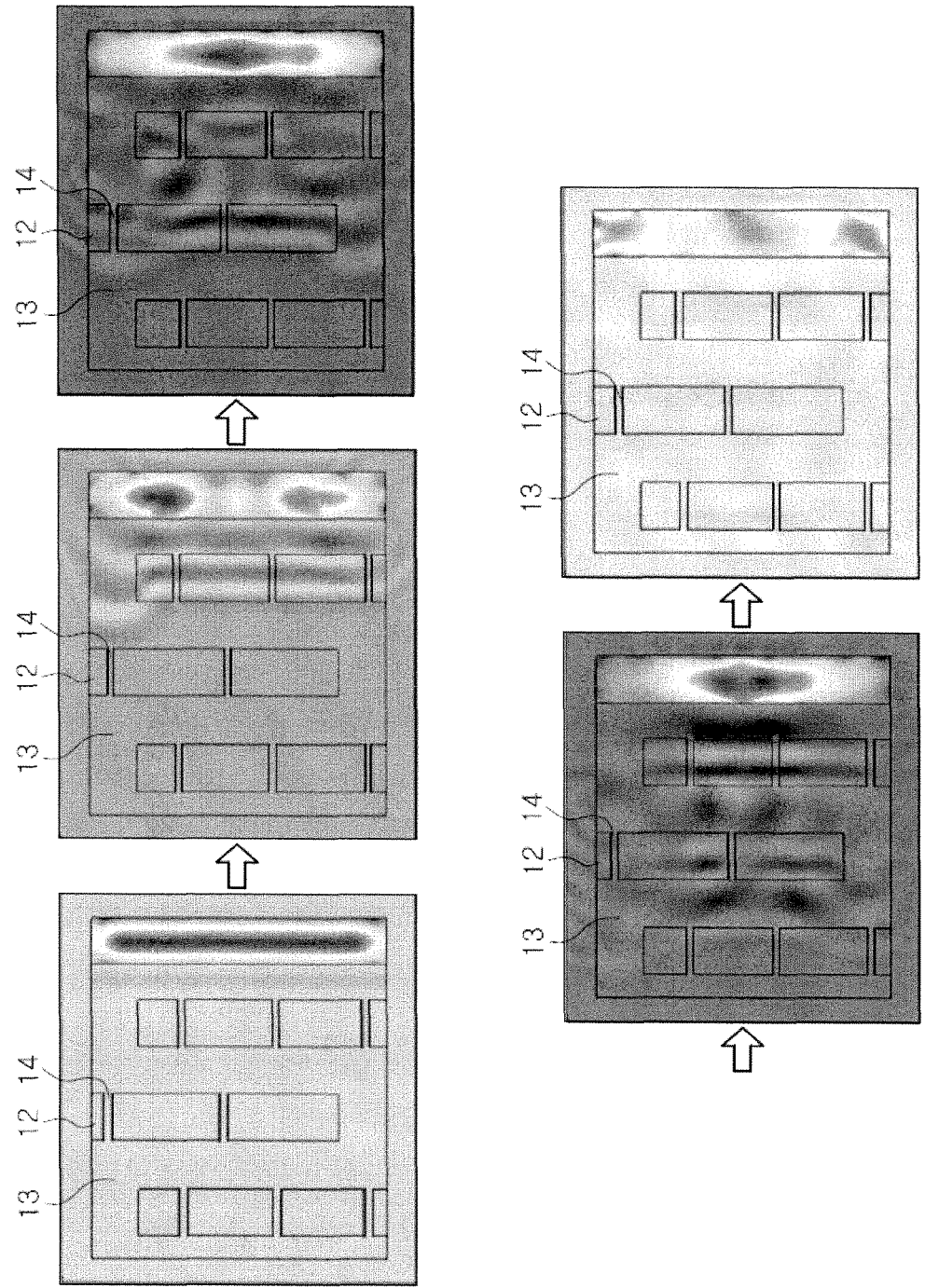
FIG. 5 is a conceptual view illustrating a state in which the backing layer including the plate-shaped carbon allotropes and the backing material symmetrically transfers heat generated in the piezoelectric layer to the rear of the ultrasonic probe of FIG. 1, in accordance with an embodiment of the present invention.

FIG. 4 is a conceptual view illustrating a state in which heat generated in the piezoelectric layer 3 is dissipated by the plate-shaped carbon allotropes 11, and FIG. 5 is a conceptual view illustrating a state in which the backing layer 10 including the plate-shaped carbon allotropes 11 and the backing material 12 symmetrically transfers heat generated in the piezoelectric layer 3 to the rear of the ultrasonic probe 1 of FIG. 1.

Referring to FIG. 4, heat 31 generated in the piezoelectric layer 3 may be transferred to the plate-shaped carbon allotropes 11 of the backing layer 10. The main frames 13 of the plate-shaped carbon allotropes 11 may absorb the heat transferred from the piezoelectric layer 3, and may form a main heat flow 32 along the main frames 13, and the main heat flow 32 may descend toward a lower side of the plate-shaped carbon allotropes 11. Also, a heat flow that deviates from the main heat flow 32 may be transferred to the support frames 14 of the plate-shaped carbon allotropes 11. The heat flow that is transferred to the support frames 14 of the plate-shaped carbon allotropes 11 may form a sub heat flow 33, and the sub heat flow 33 may be combined with the main heat flow 32 in a downward direction.

Heat that descends toward the lower side of the plate-shaped carbon allotropes 11 along the main heat flow 32 and the sub heat flow 33 may be dissipated to a left side of the plate-shaped carbon allotropes 11 while descending so that left heat dissipation 34 can be preformed, and may be dissipated to a right side of the plate-shaped carbon allotropes 11 so that right heat dissipation 35 can be performed. Also, the descending heat may be transferred and dissipated to the lower side of the plate-shaped carbon allotropes 11 so that lower heat dissipation 36 can be performed.

Referring to FIG. 5, heat generated in the left piezoelectric layer 3 may be transferred to the left side of the plate-shaped carbon allotropes 11 along the plate-shaped carbon allotropes 11 including the main frames 13 and the support frames 14 over time.

Since the plate-shaped carbon allotropes 11 and the backing material 12 are provided in the piezoelectric layer 3 to be top and bottom symmetrical with respect to each other, heat that is generated in the piezoelectric layer 3 and absorbed by the backing layer 10 may proceed to the left side of the plate-shaped carbon allotropes 11 to be top and bottom symmetrical with respect to each other. Also, heat that is absorbed over time may be dissipated to the left side, the upper side, and the lower side of the plate-shaped carbon allotropes 11 so that the heat in the backing layer 10 can be reduced.

Hereinafter, acoustic materials each having acoustic impedance provided between the carbon allotropes 11, in accordance with an embodiment of the present invention will be described with reference to FIG. 6.

Figure 6:
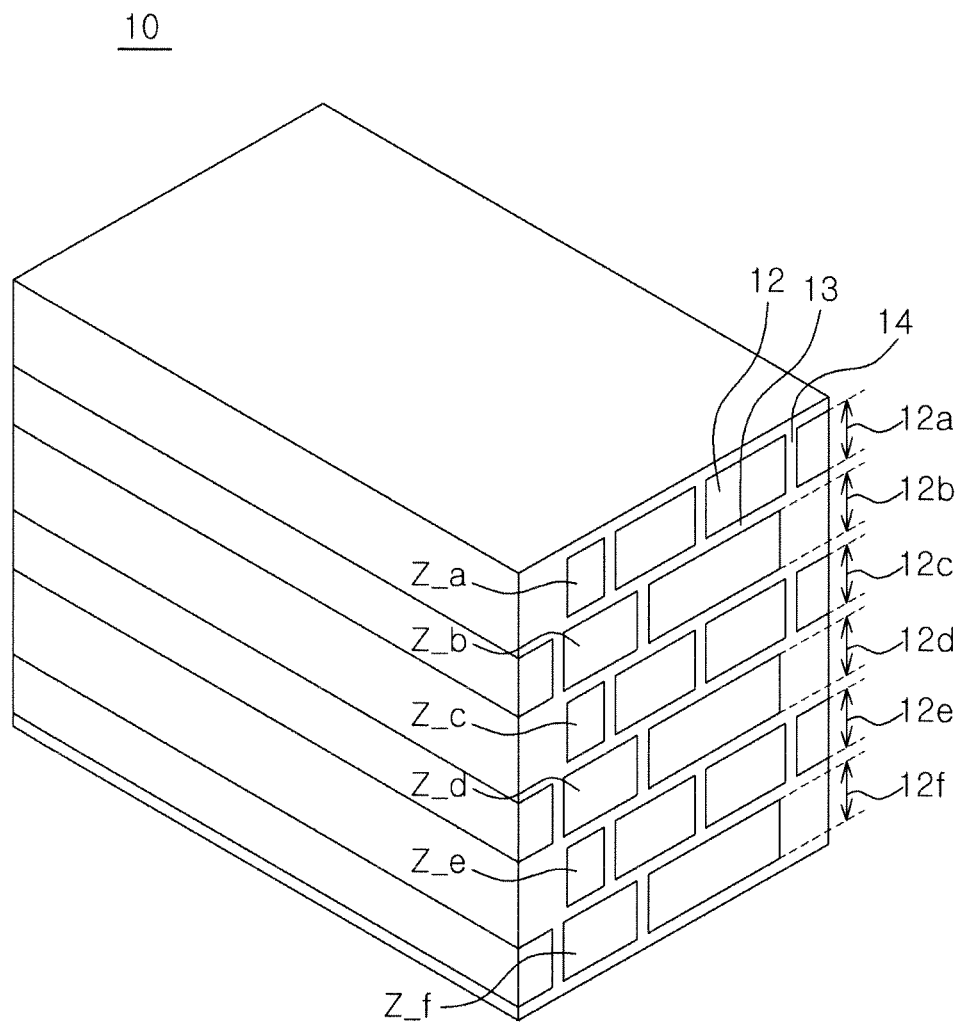
FIG. 6 is a perspective view illustrating an exterior of backing materials provided in layers, in accordance with an embodiment of the present invention.

FIG. 6 illustrates the exterior of backing materials provided in layers.

As described above, the backing materials have eigen acoustic impedance. Acoustic impedance may be a variable for attenuating ultrasonic waves and vibration that proceed to the rear of the ultrasonic probe 1.

The backing materials 12 filled in the empty space of the backing layer 10 other than the plate-shaped carbon allotropes 11 may be determined according to performance and other variables of the ultrasonic probe 1.

For example, the backing materials 12 may be filled in layers to have the same acoustic impedance so that sound layers may have uniform sound absorption performance. That is, acoustic impedance of the backing materials 12 filled in a first layer 12a, a second layer 12b, a third layer 12c, a fourth layer 12d, a fifth layer 12e, and a sixth layer 12f of FIG. 6 may be the same ($Z\_a = Z\_b = Z\_c = Z\_d = Z\_e = Z\_f$).

Also, when intensities of ultrasonic waves and vibration that proceed to the rear of the piezoelectric layer 3 are strong, the backing materials 12 may be filled in layers so that acoustic impedance of the backing materials 12 can be reduced from a top surface to a bottom surface of the backing layer 10.

In detail, when, in terms of acoustic impedance of the backing materials 12 filled in layers of FIG. 6, when acoustic impedance of the first layer 12a is $Z\_a$, acoustic impedance of the second layer 12b is $Z\_b$, acoustic impedance of the third layer 12c is $Z\_c$, acoustic impedance of the fourth layer 12d is $Z\_d$, acoustic impedance of the fifth layer 12e is $Z\_e$, and acoustic impedance of the sixth layer 12f is $Z\_f$, the acoustic impedance $Z\_a$ of the first layer 12a may be greater than the acoustic impedance $Z\_b$ of the second layer 12b, and the acoustic impedance $Z\_b$ of the second layer 12b may be greater than the acoustic impedance $Z\_c$ of the third layer 12c, and the acoustic impedance $Z\_c$ of the third layer 12c may be greater than the acoustic impedance $Z\_d$ of the fourth layer 12d. Also, the acoustic impedance $Z\_d$ of the fourth layer 12d may be greater than the acoustic impedance $Z\_e$ of the fifth layer 12e, and the acoustic impedance $Z\_e$ of the fifth layer 12e may be greater than the acoustic impedance $Z\_f$ of the sixth layer 12f ($Z\_a > Z\_b > Z\_c > Z\_d > Z\_e > Z\_f$).

Also, when the intensities of ultrasonic waves and vibration that proceed to the rear of the piezoelectric layer 3 are weak, the backing materials 12 may be filled in layers so that acoustic impedance of the backing materials 12 can increase from the top surface to the bottom surface of the backing layer 10.

In detail, the acoustic impedance $Z\_a$ of the first layer 12a may be less than the acoustic impedance $Z\_b$ of the second layer 12b, and the acoustic impedance $Z\_b$ of the second layer 12b may be less than the acoustic impedance $Z\_c$ of the third layer 12c, and the acoustic impedance $Z\_c$ of the third layer 12c may be less than the acoustic impedance $Z\_d$ of the fourth layer 12d. Also, the acoustic impedance $Z\_d$ of the fourth layer 12d may be less than the acoustic impedance $Z\_e$ of the fifth layer 12e, and the acoustic impedance $Z\_e$ of the fifth layer 12e may be less than the acoustic impedance $Z\_f$ of the sixth layer 12f ($Z\_a < Z\_b < Z\_c < Z\_d < Z\_e < Z\_f$).

In addition, the acoustic impedance of the backing materials 12 filled in layers in the backing layer 10 may be an example in which the type of the backing materials 12 filled using various methods for improving sound absorption performance is determined according to the performance of the ultrasonic probe 1.

Hereinafter, an attenuation capability of the backing layer 10 that attenuates ultrasonic waves that proceed to the rear of the piezoelectric layer 3, in accordance with an embodiment of the present invention will be described with reference to FIGS. 7A and 7B.

Figure 7A:
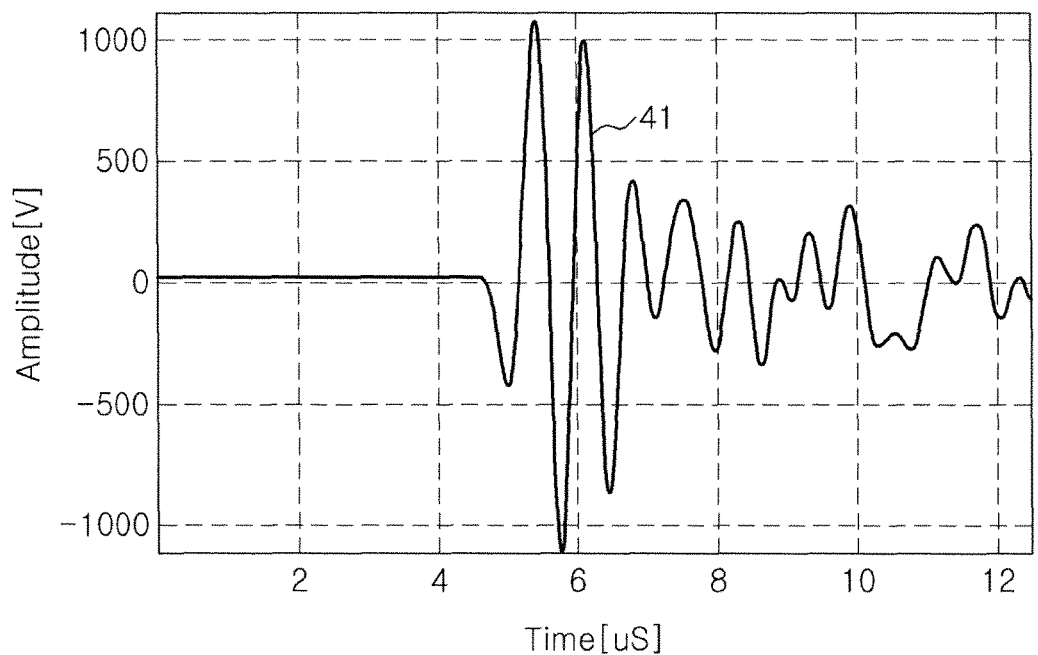
FIG. 7A is a graph showing a state in which ultrasonic waves that proceed toward the backing layer are attenuated over time of the backing layer including plate-shaped carbon allotropes, in accordance with an embodiment of the present invention.
Figure 7B:
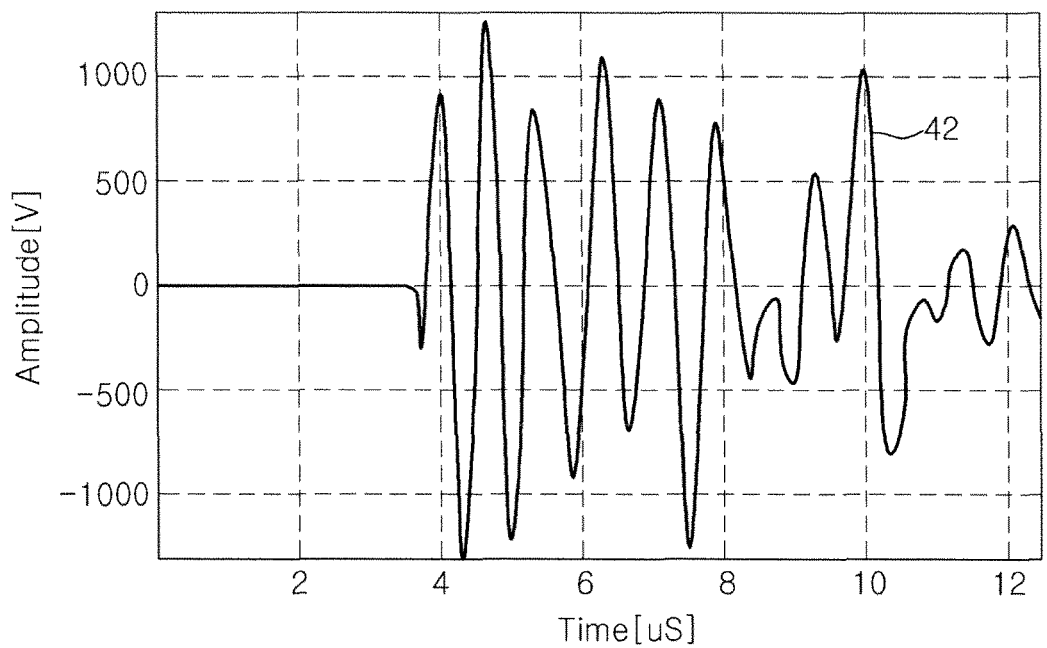
FIG. 7B is a graph showing a state in which ultrasonic waves that proceed toward the backing layer are attenuated over time of the backing layer including cylindrical carbon allotropes, in accordance with an embodiment of the present invention.

FIG. 7A is a graph showing a state in which ultrasonic waves that proceed toward the backing layer are attenuated over time of the backing layer including the plate-shaped carbon allotropes 11, and FIG. 7B is a graph showing a state in which ultrasonic waves that proceed toward the backing layer are attenuated over time of the backing layer including cylindrical carbon allotropes, in accordance with an embodiment of the present invention.

Examining the attenuation capability of the backing layer including the plate-shaped carbon allotropes 11 as shown in FIG. 7A, ultrasonic waves that proceed to the rear of the piezoelectric layer 3 are introduced into the backing layer at about 5 [uS], and as time elapses, an amplitude 41 [V] corresponding to the Y-axis is reduced. When the graph of FIG. 7A is converted into a log scale, the attenuation capability may be about 46.78 [dB].

However, examining the attenuation capability of the backing layer including the cylindrical carbon allotropes as shown in FIG. 7B, ultrasonic waves that proceed to the rear of the piezoelectric layer 3 are introduced into the backing layer at about 5 [uS], and as time elapses, an amplitude 42 [V] corresponding to the Y-axis is reduced. However, the amplitude 42 [V] has a lower attenuation rate than that of the amplitude 41 [V] of the backing layer including the plate-shaped carbon allotropes 11. When the graph of FIG. 7B is converted into a log scale, the attenuation capability may be about 48.19 [dB].

That is, the attenuation capability of the backing layer including the plate-shaped carbon allotropes 11 may be about 46.78 [dB], and the attenuation capability of the backing layer including the cylindrical carbon allotropes may be about 48.19 [dB]. Thus, the attenuation capability of the backing layer including the plate-shaped carbon allotropes 11 may be about 2.8 [dB] higher than that of the backing layer including the cylindrical carbon allotropes.

Hereinafter, an embodiment in which a plurality of piezoelectric layers 3 are arranged, will be described with reference to FIG. 8.

The plurality of piezoelectric layers 3 may be provided on the top surface of the backing layer including an array. The plurality of piezoelectric layers 3 connected to the array may be arranged using various methods according to the object to be inspected and the purpose of the ultrasonic probe 1 and for other reasons. For example, the plurality of piezoelectric layers 3 may be arranged in one shape selected from the group consisting of a matrix shape, a linear shape, a convex shape, and a concave shape.

Figure 8:
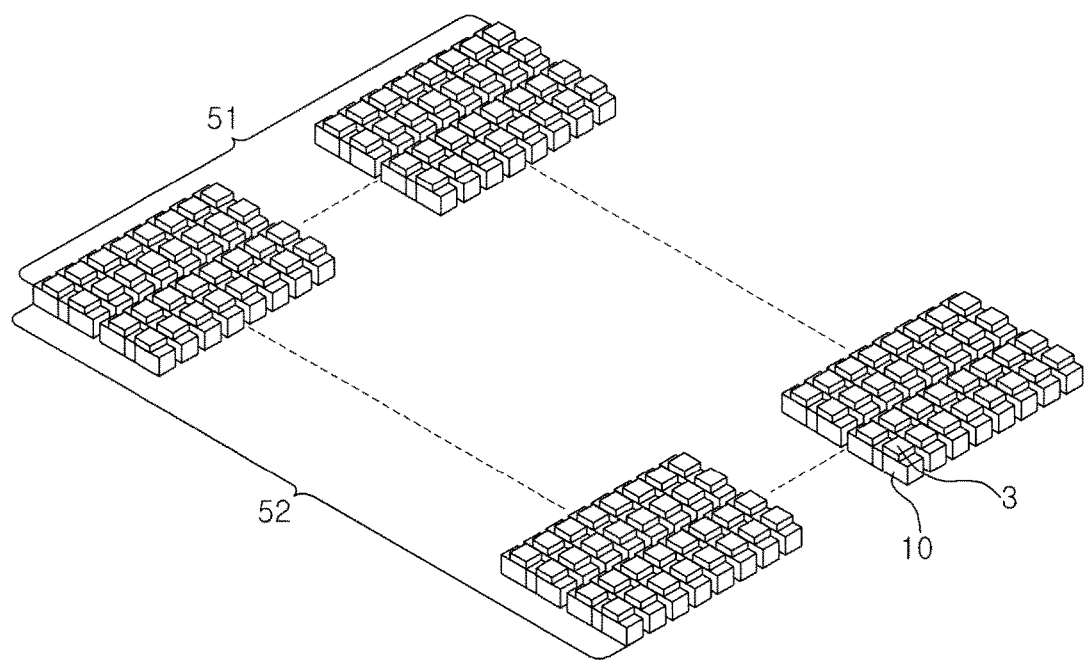
FIG. 8 is a perspective view of a piezoelectric layer arranged in the form of a two-dimensional (2D) matrix in accordance with an embodiment of the present invention.

FIG. 8 is a perspective view of the piezoelectric layer 3 arranged in the form of a two-dimensional (2D) matrix.

For example, 144 piezoelectric layers 3 may be arranged on a horizontal axis 51 of an array, and 72 piezoelectric layers 3 may be arranged on a vertical axis 52 of the array. Thus, the piezoelectric layers 3 may be arranged in the form of a 144×72 2D matrix so that total 10,368 piezoelectric layers may be arranged.

However, the above-mentioned arrangement of the 144× 72 2D matrix does not limit the number of 2D matrix arrangements, and the piezoelectric layers 3 may be arranged to have various numbers using various methods according to the object to be inspected and the purpose of the ultrasonic probe 1 and for other reasons.

Hereinafter, a method of manufacturing the ultrasonic probe 1 including the plate-shaped carbon allotropes 11, in accordance with an embodiment of the present invention will be described with reference to FIG. 9.

Figure 9:
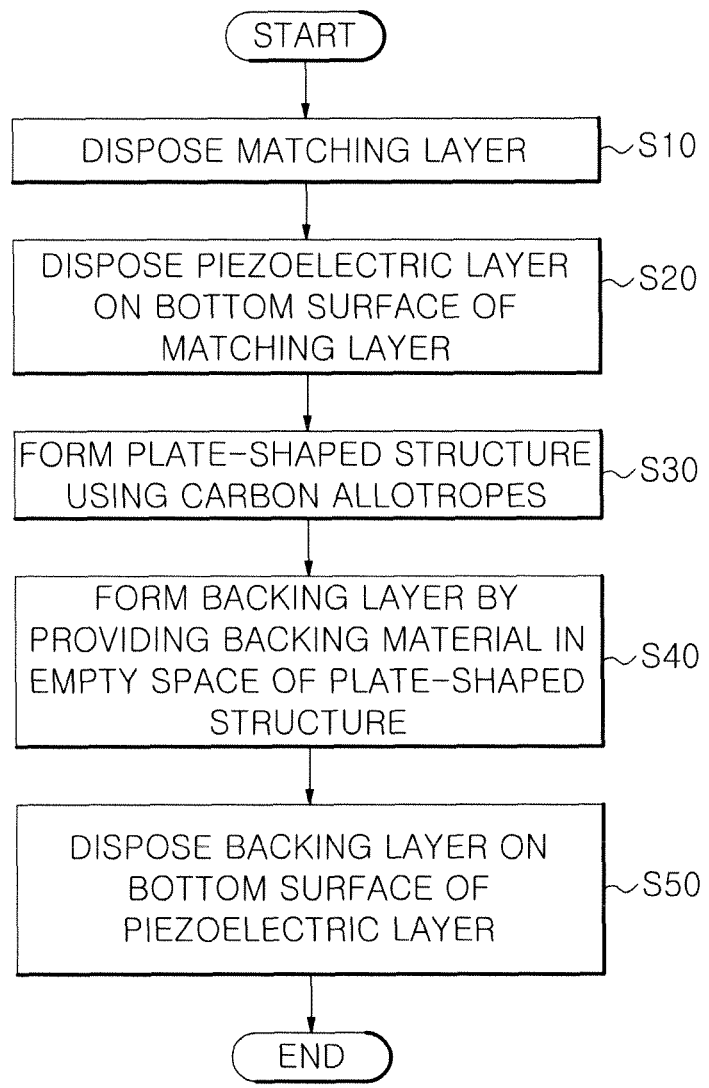
FIG. 9 is a flowchart illustrating a method of manufacturing an ultrasonic probe including plate-shaped carbon allotropes, in accordance with an embodiment of the present invention.

FIG. 9 illustrates a time sequential order for manufacturing the ultrasonic probe 1 including the plate-shaped carbon allotropes 11.

First, a matching layer may be disposed (S10), and a piezoelectric layer that transmits and receives ultrasonic waves may be disposed on a bottom surface of the matching layer (S20).

A structure is formed by processing carbon allotropes in a plate shape using back grinding, dicing, etching, or other methods (S30), and backing materials may be provided in an empty space of a backing layer other than the plate-shaped structure so that the backing layer can be formed (S40).

Last, the backing layer is provided on a bottom surface of the piezoelectric layer (S50) so that the ultrasonic probe 1 can be manufactured.

As described above, in an ultrasonic probe and a method of manufacturing the ultrasonic probe according to the one or more embodiments of the present invention, heat transfer efficiency in which an attenuation capability of a backing layer is maintained and heat generated in a piezoelectric layer is transferred to the rear of the ultrasonic probe and is dissipated, can be improved.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. An ultrasonic probe comprising:
a matching layer;
a piezoelectric layer that is disposed on a bottom surface of the matching layer and generates ultrasonic waves; and
a backing layer that is disposed on a bottom surface of the piezoelectric layer and comprises plate-shaped carbon allotropes and a backing material provided between the plate-shaped carbon allotropes,
wherein the backing layer comprises a plurality of layers which are formed in a parallel direction to the piezoelectric layer,
wherein the carbon allotropes include: a main frame stacked in the parallel direction to the piezoelectric layer on each of the layers of the backing layer; and a plurality of support frames formed in a vertical direction to the piezoelectric layer on each of the layers of the backing layer,
wherein the plurality of support frames on each layer of the plurality of layers of the backing layer are staggered relative to the plurality of support frames on adjacent layers of the plurality of layers of the backing layer disposed thereabove or therebelow,
wherein the main frame includes:
horizontal frames, which are parallel to the backing layer; and
vertical frames, which are perpendicular to the backing layer and disposed between the horizontal frames to support the horizontal frames, and
wherein the vertical frames are disposed between ends of two adjacent horizontal frames among the horizontal frames alternately in a zig-zag shape so that other ends of the two adjacent horizontal frames are alternately open.

2. The ultrasonic probe of claim 1, wherein the plurality of layers of the backing layer include a first layer and a second layer,
wherein the plurality of the support layers include: a first support frame formed on the first layer; and a second support frame formed on the second layer, and
wherein the first support frame is formed in a different position from that of the second support frame.

3. The ultrasonic probe of claim 1, wherein the backing material provided between the carbon allotropes each have a same acoustic impedance in each layer of the backing layer.

4. The ultrasonic probe of claim 1, wherein the backing material is provided so that an acoustic impedance of the backing material provided between the carbon allotropes is reduced from a top surface to a bottom surface of the backing layer.

5. The ultrasonic probe of claim 1, wherein the backing material is provided so that an acoustic impedance of the backing material provided between the carbon allotropes increases from the top surface to the bottom surface of the backing layer.

6. The ultrasonic probe of claim 1, wherein the plate-shaped carbon allotropes are one selected from the group consisting of carbon nanotubes (CNTs), graphene, and graphite.

7. The ultrasonic probe of claim 1, wherein the plate-shaped carbon allotropes are a synthetic material of the carbon allotropes and a metal.

8. The ultrasonic probe of claim 1, wherein a plurality of piezoelectric layers are arranged in one shape selected from the group consisting of a matrix shape, a linear shape, a convex shape, and a concave shape.

9. A method of manufacturing an ultrasonic probe, the method comprising:
disposing a matching layer;
disposing a piezoelectric layer that generates ultrasonic waves, on a bottom surface of the matching layer;

forming a backing layer by providing a backing material between plate-shaped carbon allotropes; and disposing the backing layer on a bottom surface of the piezoelectric layer, wherein the forming the backing layer comprises:

forming a plurality of layers of the backing layer in a parallel direction to the piezoelectric layer, stacking a main frame in the parallel direction to the piezoelectric layer on each of the layers of the backing layer, and forming a plurality of support frames in a vertical direction to the piezoelectric layer on each of the layers of the backing layer, wherein the plurality of support frames on each layer of the plurality of layers of the backing layer are staggered relative to the plurality of support frames on adjacent layers of the plurality of layers of the backing layer disposed thereabove or therebelow, wherein the main frame includes:
  horizontal frames, which are parallel to the backing layer; and
  vertical frames, which are perpendicular to the backing layer and disposed between the horizontal frames to support the horizontal frames, and wherein the vertical frames are disposed between ends of two adjacent horizontal frames among the horizontal frames alternately in a zig-zag shape so that other ends of the two adjacent horizontal frames are alternately open.

10. The method of claim 9, wherein the forming the plurality of layers of the backing layer includes forming a first layer and a second layer, the forming the plurality of the support layers includes forming a first support frame on the first layer and a second support frame on the second layer, and the forming the first support frame includes forming the first support frame in a different position from that of the second support frame.

11. The method of claim 9, wherein the forming of the backing layer comprises providing a backing material between the carbon allotropes to have a same acoustic impedance in each layer of the backing layer.

12. The method of claim 9, wherein the forming of the backing layer comprises providing a backing material so that an acoustic impedance of the backing material provided between the carbon allotropes is reduced from a top surface to a bottom surface of the backing layer.

13. The method of claim 9, wherein the forming of the backing layer comprises providing a backing material so that an acoustic impedance of the backing material provided between the carbon allotropes increases from the top surface to the bottom surface of the backing layer.

14. The method of claim 9, wherein the plate-shaped carbon allotropes use one selected from the group consisting of carbon nanotubes (CNTs), graphene, and graphite.

15. The method of claim 9, wherein the plate-shaped carbon allotropes use a synthetic material of the carbon allotropes and a metal.

16. The method of claim 9, wherein the disposing of the piezoelectric layer comprises arranging a plurality of piezoelectric layers in one shape selected from the group consisting of a matrix shape, a linear shape, a convex shape, and a concave shape.

* * * * *